US011154243B2

(12) United States Patent
Esposito et al.

(10) Patent No.: US 11,154,243 B2
(45) Date of Patent: Oct. 26, 2021

(54) SENSOR SYSTEMS FOR USER-SPECIFIC EVALUATION OF GAIT, FOOTWEAR AND GARMENT FITTING; MONITORING OF CONTACT, FORCE, PRESSURE AND/OR SHEAR AT OR NEAR BODY SURFACES

(71) Applicant: Sensoria Inc., Redmond, WA (US)

(72) Inventors: Mario Esposito, Redmond, WA (US); Victoria Esposito, Redmond, WA (US); Maurizio Macagno, Redmond, WA (US); Davide Giancarlo Vigano', Redmond, WA (US); Maria Pia Carmagnani, Redmond, WA (US); Roberto Reif, Seattle, WA (US)

(*) Notice: Subject to any disclaimer, the term of this patent is extended or adjusted under 35 U.S.C. 154(b) by 507 days.

(21) Appl. No.: 15/133,124

(22) Filed: Apr. 19, 2016

(65) Prior Publication Data

US 2016/0367191 A1    Dec. 22, 2016

Related U.S. Application Data

(60) Continuation-in-part of application No. 14/908,502, filed on Jan. 28, 2016, now abandoned, which is a
(Continued)

(51) Int. Cl.
*A61B 5/103* (2006.01)
*A61B 5/00* (2006.01)
(Continued)

(52) U.S. Cl.
CPC ............ *A61B 5/6807* (2013.01); *A43D 1/027* (2013.01); *A61B 5/0022* (2013.01); *A61B 5/01* (2013.01);
(Continued)

(58) Field of Classification Search
CPC ...... A43D 1/02; A43D 2200/60; A43D 1/027; A61B 5/1036; A61B 5/112;
(Continued)

(56) References Cited

U.S. PATENT DOCUMENTS 8,694,080 B2 * 4/2014 Farrior ................. A61B 5/0402
600/509
9,817,439 B2 * 11/2017 Gosieski, Jr. ....... G06F 17/5086
(Continued)

FOREIGN PATENT DOCUMENTS

WO   WO-2015017712 A1 *  2/2015 ........... A61B 5/1038
WO   WO 2015/169942 A1 * 11/2015

OTHER PUBLICATIONS

Fukahori, et al. "Exploring subtle foot plantar-based gestures with sock-placed pressure sensors." Proceedings of the 33rd Annual ACM Conference on Human Factors in Computing Systems. ACM, 2015.*
(Continued)

*Primary Examiner* — David J. McCrosky

(57) ABSTRACT

Sensing devices including flexible and stretchable pressure sensors may be associated with or incorporated in garments intended to be worn against a body surface (directly or indirectly), or may be associated with other types of flexible substrates. Systems and methods for storing, communicating, processing, analyzing and displaying data collected by sensor components for remote monitoring of conditions at or near body surfaces are also disclosed. Sensors and sensor systems provide substantially real-time feedback relating to current body conditions and may provide user-specific feedback relating to gait and footwear fit and performance, facilitating improved footwear matching to individual users
(Continued)

and improved footwear design and manufacturing, and enabling early intervention when conditions indicate intervention is appropriate.

17 Claims, 6 Drawing Sheets

Related U.S. Application Data continuation-in-part of application No. 14/588,363, filed on Dec. 31, 2014, now abandoned, which is a continuation-in-part of application No. 14/574,220, filed as application No. PCT/US2014/049263 on Jul. 31, 2014, now abandoned, which is a division of application No. 13/753,456, filed on Jan. 29, 2013, now Pat. No. 8,925,392.

(60) Provisional application No. 62/150,049, filed on Apr. 20, 2015, provisional application No. 61/923,161, filed on Jan. 2, 2014, provisional application No. 61/860,869, filed on Jul. 31, 2013, provisional application No. 61/747,877, filed on Dec. 31, 2012, provisional application No. 61/592,333, filed on Jan. 30, 2012.

(51) Int. Cl.

| | |
|---|---|
| *A43D 1/02* | (2006.01) |
| *G01L 1/18* | (2006.01) |
| *A61B 5/024* | (2006.01) |
| *A61B 5/11* | (2006.01) |
| *A61B 5/01* | (2006.01) |
| *D04B 1/14* | (2006.01) |
| *A41D 1/00* | (2018.01) |
| *G16H 40/67* | (2018.01) |
| *A61B 5/08* | (2006.01) |
| *A61B 5/021* | (2006.01) |
| *G16H 40/63* | (2018.01) |

(52) U.S. Cl.
CPC ............ *A61B 5/024* (2013.01); *A61B 5/1038* (2013.01); *A61B 5/11* (2013.01); *D04B 1/14* (2013.01); *G01L 1/18* (2013.01); *A41D 1/002* (2013.01); *A43D 2200/60* (2013.01); *A61B 5/002* (2013.01); *A61B 5/021* (2013.01); *A61B 5/0816* (2013.01); *A61B 5/447* (2013.01); *A61B 5/6831* (2013.01); *A61B 2560/0223* (2013.01); *A61B 2560/045* (2013.01); *A61B 2562/0247* (2013.01); *A61B 2562/222* (2013.01); *A61B 2562/227* (2013.01); *D10B 2401/18* (2013.01); *D10B 2403/02431* (2013.01); *G16H 40/63* (2018.01); *G16H 40/67* (2018.01)

(58) Field of Classification Search
CPC ...... A61B 2562/0247; A61B 2562/046; A61B 5/1038; A61B 2562/221; A61B 2562/222; A43B 3/0005; G06F 17/5086; G06F 1/163; G06F 2217/32; G06F 3/011; G06Q 30/02; G06Q 30/0621; G06Q 30/0201; G06Q 30/0282; G06Q 30/0627; G06Q 30/0629; G06Q 30/0631; G06Q 30/0641; A63F 13/218; A63F 2300/1012; G06K 9/00348
See application file for complete search history.

(56) References Cited

U.S. PATENT DOCUMENTS

| | | | | |
|---|---|---|---|---|
| 10,013,803 | B2* | 7/2018 | Mach Shepherd | ..... G06T 17/00 |
| 2003/0110095 | A1* | 6/2003 | Danenberg | ............... A43D 1/02 |
| | | | | 705/26.64 |
| 2007/0011173 | A1* | 1/2007 | Agostino | ................. A43D 1/02 |
| 2011/0015498 | A1* | 1/2011 | Mestrovic | ........... A61B 5/1038 |
| | | | | 600/301 |
| 2016/0252412 | A1* | 9/2016 | McMillen | ........... A43B 3/0005 |
| | | | | 73/774 |
| 2017/0180067 | A1* | 6/2017 | Poornachandran | .... G06Q 10/02 |

OTHER PUBLICATIONS

C. Yang et al., "A wireless gait analysis system by digital textile sensors," 2009 Annual International Conference of the IEEE Engineering in Medicine and Biology Society, Minneapolis, MN, 2009, pp. 7256-7260.*

T. Holleczek, et al, "Textile pressure sensors for sports applications," SENSORS, 2010 IEEE, Kona, HI, 2010, pp. 732-737.*

Internet Archive, Novel.de, "Pedar" Jan. 7, 2015. Retrieved from <https://web.archive.org/web/20150107212220/http://novel.de/novelcontent/pedar> on Jun. 10, 2019 (Year: 2015).*

* cited by examiner

SENSOR SYSTEMS FOR USER-SPECIFIC EVALUATION OF GAIT, FOOTWEAR AND GARMENT FITTING; MONITORING OF CONTACT, FORCE, PRESSURE AND/OR SHEAR AT OR NEAR BODY SURFACES

REFERENCE TO RELATED PATENT APPLICATIONS

This application claims priority to U.S. Patent Application 62/150,049, filed Apr. 20, 2015 and is a continuation-in-part of U.S. patent application Ser. No. 14/574,220 filed Dec. 17, 2014, which is a divisional application of U.S. patent application Ser. No. 13/753,456, filed Jan. 29, 2013, which claims priority to U.S. Provisional Patent Application No. 61/592,333, filed Jan. 30, 2012 and U.S. Provisional Patent Application No. 61/747,877 filed Dec. 31, 2012. This application is also a continuation-in-part of U.S. patent application Ser. No. 14/908,502, filed Jan. 28, 2016, which is a 371 national phase entry of PCT/US14/049263, filed Jul. 31, 2014, which claims priority to U.S. Patent Application 61/860,869 filed Jul. 31, 2013. This application is also a continuation-in-part of U.S. patent application Ser. No. 14/588,363, filed Dec. 31, 2014, which claims priority to U.S. Patent Application 61/923,161 filed Jan. 2, 2014. The disclosures of the previously referenced applications are incorporated by reference herein in their entireties.

FIELD

The present invention relates generally to sensor systems that may be associated with or incorporated in footwear, garments and other items intended to be worn against a body surface (directly or indirectly). Systems and methods for collecting, storing, communicating, processing, analyzing and displaying data and analytics for monitoring conditions at body surfaces are also disclosed.

BACKGROUND

Various types of sensing systems have been incorporated in shoes, insoles, socks and garments for monitoring physiological parameters for various applications, including recreational, sporting, military, diagnostic and medical applications. Vital sign monitoring using various types of sensing systems, including fabric electrodes incorporated in garments, are known. Medical applications for sensing pressure, temperature and the like for purposes of monitoring neuropathic and other degenerative conditions with the goal of alerting individual and/or medical service providers to sensed parameters that may indicate the worsening of a condition, lack of healing, and the like, have been proposed. Footwear-related sensing systems designed to provide sensory data for patients suffering from neuropathy, for gait analysis, rehabilitation assessment, monitoring athletic and fitness activities, and the like, have been proposed. Gait analysis may be particularly important for monitoring athletic and fitness activities, and for monitoring individuals with various types of injuries who may be at risk for falling. Accurate gait analysis may be used to detect injuries and falling incidents, and to predict the likelihood or onset of injury, as well as the likelihood of falling.

U.S. Patent Publication 2011/0015498, for example, discloses a system, garment and method implementing sensors that can be used for measuring or monitoring pressure or forces exerted on the feet, the stumps of limbs of an amputee, or other body parts subject to forces, and on pressure bandages. These systems may be used, for example, for recreational, sporting, military and medical applications and may be used in the treatment of neuropathic or other degenerative conditions.

Comfort is a highly subjective and often elusive quality. The comfort of footwear, garments, prostheses, and the like, may vary and change based on any acute or chronic conditions experienced by the user, localized physiological conditions, changing body sizes, shapes, conditions, and the like. And, it is difficult to accurately gauge the comfort of footwear and garments based on a very short trial period. Identifying and locating comfortable footwear and garments is challenging, moreover, because the footwear and garment industries are dynamic and changes in styles, materials, manufacturing techniques, manufacturing facilities, and the like, all affect the fit and comfort of footwear and garments.

It is thus difficult to reliably anticipate and accurately judge the "fit" of various types and styles of footwear and garments given the many variables and short trial period, and this results in a relatively high rate of returned products. It is even more difficult to anticipate the fit of various types and styles of footwear and garments purchased from remote locations or e-commerce websites, when it is not possible to trial footwear and garments prior to purchase. The number of purchases made remotely without the ability to physically "try on" footwear and garments is increasing rapidly and the high rate of poor fits and returns incurs significant costs to both buyers and sellers.

Methods and systems described herein are thus directed to providing sensor-based systems that may be conveniently worn or applied by a user to provide feedback relating to user-specific information concerning contact, pressure and/or force and/or shear exerted at or near spatially identified body surfaces. Methods and systems described herein are also directed to applying data processing and analytics to data collected from the sensor-based systems.

SUMMARY

In one aspect, sensor systems of the present invention comprise at least one and preferably a plurality of force and/or pressure and/or shear sensor(s) (referred to herein simply as "pressure sensor(s)") mounted to or incorporated in or integrated in or associated with (referred to herein, collectively, as "associated with") a flexible and pliable substrate material such as a fabric substrate in the form of a wearable garment or a portion of a wearable garment (e.g. a sock, shirt, sleeve, or other type of garment), a wearable band, or an independently positionable component that can be mounted to a body surface. In some embodiments, one or more pressure sensor(s) may be associated with a substrate that may not be highly flexible, such as a shoe component (e.g., a midsole or sole or upper component), a permanent or removable insole or orthotic component, or the like. Various aspects of sensing systems and background relating to the construction and use of and utility for such sensing systems are described in the following previously published and commonly owned patent publications, all of which are incorporated herein by reference in their entireties: U.S. Pat. Nos. 8,925,392 and 9,186,092; PCT Patent Publication 2013/116242 A2; PCT Patent Publication 2015/017712 A1; U.S. Patent Publication US-2015-0182843-A1; and PCT Patent Publication WO 2015/175838 A1.

In general, pressure sensor(s) described herein may be associated with any type of substrate that contacts the body, directly or indirectly. Thus, pressure sensor(s) and sensor systems described herein, including e-textile pressure sensors and a variety of other types of sensors, with suitable leads and conductive traces, may be associated with a variety of substrates including, without limitation, garments intended to be worn (directly or indirectly) against the skin of an individual, such as a shirt or tunic, underwear, leggings, socks, footies, gloves, caps, bands such as wrist bands, leg bands, torso and back bands, brassieres, and the like. Pressure sensors and sensor systems may additionally be associated with bands and/or wraps having different sizes and configurations for fitting against or wrapping around a portion of an individual's body, and with compression garments, bandages, wound dressing materials, as well as with other types of accessories that contact a user's body surface (directly or indirectly) such as insoles, shoes, boots, belts, straps, and the like.

The pressure sensor(s) and sensor systems described herein provide objective data relating to pressure and/or force or and/shear (or measurements or values that are derivative thereof) at identifiable spatial locations on or near a body surface where the sensor(s) are positioned. Signals collected at pressure sensor sites are conveyed to a host data processing system for data processing and analysis, optionally through one or more electronic intermediates, and user-specific data, analytics, recommendations, and the like, may be communicated directly to the user, or to an intermediate for analysis, review, and/or communication to the user. The sensor(s) and sensor systems may therefore be used to evaluate how well a shoe, prosthetic, compression garment, other type of garment or the like conforms to a user's body and to provide detection and relative and/or quantitative measurements of pressure, force and/or shear at identifiable spatial locations while the user is at rest and during various activities, substantially in real time. The sensor(s) and sensor systems may also be used to detect and monitor various aspects of a user's gait, substantially in real time.

Pressure sensors employed with flexible substrates are preferably flexible and substantially conform to a body surface, and are capable of sensing force and/or pressure and/or shear exerted on the sensor, and thereby on the underlying body surface. Each sensor is electrically connected (directly or indirectly) to a flexible conductive trace associated with the substrate. Conductive traces terminate at conductive signal transfer terminals, which may be associated with the substrate or with a sensor assembly. One or more of the sensor(s) and conductive traces may be stretchable and/or elastic as well as being flexible.

In some embodiments, the pressure sensor(s) may comprise flexible resistive and/or conductive materials such as resistive or conductive textile materials. Suitable flexible resistive fabric materials are available, for example, from VTT/Shieldex Trading USA, 4502 Rt-31, Palmyra, N.Y. 14522, from Statex Productions & Vertriebs GmbH, Kleiner Ort 11 28357 Bremen Germany, and from Eeonyx Corp., 750 Belmont Way, Pinole, Calif. 94564. Sensors comprising e-textile materials may be associated with a substrate or carrier layer, or they may be woven into or integrated in the material of the substrate. In some embodiments, the pressure sensor(s) may comprise other types of flexible conductive or resistive materials, such as resistive or conductive thermoplastic elastomers (TPEs), resistive or conductive inks, resistive or conductive silicon-containing materials, or other flexible resistive or conductive materials that may be applied directly to a substrate, or that may be applied to a carrier layer, forming a sensor assembly that may be bonded or adhered to a substrate.

In some embodiments, the conductive traces may comprise flexible electrically conductive materials, such as conductive textile materials, conductive threads, yarns, or the like that may be associated with a substrate or carrier layer or woven into or integrated in the material of the substrate. In some embodiments, the conductive traces may comprise other types of flexible conductive materials, such as thermoplastic elastomers (TPEs), conductive inks, conductive silicon-containing materials or other flexible conductive materials that may be applied directly to a substrate, or that may be applied to a carrier layer, forming a sensor assembly that may be bonded or adhered to a substrate. Garments and accessories incorporating such sensor systems and sensor assemblies may be comfortably worn by users in many conditions, providing real time monitoring of conditions at or near body surfaces.

The signal transfer terminal(s) associated with the substrate may be matingly received in signal receipt terminals associated with a Dedicated Electronic Device (DED) that is attachable to the substrate and serves as a (temporary or permanent) data collection device. The DED may also (optionally) house batteries or other energy storage devices and serve as a sensor-charging device. The DED may communicate with one or more external electronic device(s), such as a smartphone, personal computing device/display, host computer, or the like for signal transfer, processing, analysis and display to a user and/or others. In some embodiments, the external electronic device, and/or the DED, communicates with an external, hosted computing system (operated, e.g., at a centralized, hosted facility and/or in the "Cloud") that provides additional data analysis, formulates feedback, notifications, alerts, and the like, that may be displayed to the user, a caretaker, and/or a clinician through one or more computing and/or display devices.

In some embodiments, one or more piezoresistive sensor(s) detects changes in voltage or resistance across a sensor surface area that is associated with force exerted on the sensor, which is related to pressure (as force per unit surface area) and/or shear. In some embodiments, FSR (Force Sensitive Resistor) and/or piezo-resistive sensors may be used. One type of piezoresistive force sensor that has been used previously in footwear pressure sensing applications, known as the FLEXIFORCE® sensor, can be made in a variety of shapes and sizes, and measures resistance, which is inversely proportional to applied force. These sensors use pressure sensitive inks with conductive leads terminating in pins, with the pressure sensitive area and leads sandwiched between thin, flexible film layers. FLEXIFORCE® sensors are available, for example, from Tekscan, Inc., 307 West First Street, South Boston, Mass. 02127-1309 USA. Other types of sensors may also be integrated in or associated with various substrate or carrier materials (e.g., garments, sheet materials and the like), including sensors providing data relating to temperature, moisture, humidity, stress, strain, heart rate, respiratory rate, blood pressure, blood oxygen saturation, blood flow, local gas content, bacterial content, multi-axis acceleration, positioning (GPS) and the like. A variety of such sensors is known in the art and may be adapted for use in sensing systems described herein.

Techniques for deriving force and/or pressure and/or shear measurements using e-textile sensor materials are known in the art, and various techniques may be suitable. See, e.g., http://www.kobakant.at/DIY/?p=913. Techniques for measuring other parameters using e-textile materials, such as humidity and temperature measurements, are also known and may be used in sensing systems described. See, e.g., http://www.nano-tera.ch/pdf!posters2012/

TWIGS105.pdf. E-textile pressure sensors, as described, may thus be capable of monitoring various parameters, including force, pressure, shear, humidity, temperature, and the like, at the site. Additional monitoring capabilities may be available using e-textile sensors as innovation in textile sensors proceeds and as nano-materials and materials incorporating nano-structures are developed and become commercially feasible.

The term "fabric" or "textile" or "sheet material" as used herein, may refer to many types of pliable materials, including traditional fabrics comprising woven or non-woven fibers or strands, knitted materials and materials incorporating various types of yarns, fiber reinforced sheet materials and other types of flexible sheeting materials composed of natural and/or synthetic materials, including flexible plastic sheeting material, pliable thermoplastic, foam and composite materials, screen-like or mesh materials, and the like. The underlying substrate may comprise a sheet material fabricated from flexible textile material that is stretchy and/or elastic. The sheet material forming the underlying substrate may be substantially isotropic with respect to its flexibility and/or stretch properties. By "substantially" isotropic, we mean to include materials that have no more than a 15% variation and, in some embodiments, no more than a 10% variation in flexibility and/or stretch properties in any direction, or along any axis of the material.

For garment and similar applications, for example, one or more sensor(s) and/or sensor assemblies may be mounted to (e.g., sewn or otherwise attached or connected or fixed or bonded or adhered to) or integrated in (e.g., by weaving, knitting, or the like) a surface of a fabric or textile forming a garment for contacting a user's skin, directly or indirectly, during use, and detecting pressure exerted by or against an individual's skin, or other parameters sensed at or near a skin surface. In situations where pressure or other parameters are desired to be measured as they impact an outer surface or fabric layer, one or more sensor(s) may be mounted to or integrated in an external surface of a garment.

In some embodiments, sensor(s) comprising force- and/or pressure- and/or shear-sensitive fibers, materials, sensors or the like may be sandwiched between substrate layers (as in compression garments). In some embodiments, force- and/or pressure- and/or shear-sensitive sensors may be partially or fully enclosed or encapsulated in a flexible barrier material or envelope that is substantially electrically non-conductive and fully or partially moisture resistant. In some embodiments, sensors comprising conductive or resistive thermoplastic elastomers (TPEs), conductive or resistive inks, conductive or resistive silicon, or the like materials capable of manifesting a dielectric behavior, are applied to or otherwise associated with a carrier layer (directly or indirectly) via printing or other processes. Conductive traces comprising flexible conductive materials, such as thermoplastic elastomers (TPEs), conductive inks, silicon, or the like, may likewise be applied to or otherwise associated with (directly or indirectly) a substantially electrically non-conductive and moisture resistant carrier layer via printing or other processes. In some embodiments, conductive or resistive sensors and/or conductive traces may be sandwiched between carrier layers to form a sensor assembly having a predetermined sensor arrangement and trace configuration, and such sensor assemblies may be bonded or adhered to a substrate in any desired location.

Each pressure sensor is generally associated with two leads, and each of the leads is electrically connected to a conductive trace conveying electrical signals to a signal transfer terminal. Pressure sensors as previously described may be electrically connected to leads, or they may have a flexible lead associated with or incorporated in the pressure sensor footprint. The leads are electrically connected to flexible conductive traces, which may comprise a variety of flexible conductive materials, such as conductive fabrics, conductive yarns, conductive polymers or plastics, or the like. In some embodiments, the conductive traces are stretchable and/or elastic, at least along the longitudinal axis of the conductive trace.

Each of the conductive traces terminates in a signal transfer terminal that is associated with an underlying substrate or carrier layer and can be associated with a mating signal receipt terminal of a dedicated electronic device (DED) having data storage, processing and/or analysis capabilities. In some embodiments, multiplexed signal transfer and signal receipt terminals may be utilized to accommodate multiple sets of pressure sensors using a reduced number of signal transfer and receipt terminals.

In general, conductive traces and terminals are arranged in a predetermined arrangement that corresponds to the arrangement of signal receipt terminals in the DED. Many different types and arrangements of signal transfer and receipt terminals are known and may be used in this application. In one exemplary embodiment, signal transfer and receipt terminals may be mounted in cooperating fixtures for sliding engagement of the terminals. In another embodiment, signal transfer terminals may be provided as conductive fixtures that are electrically connected to conductive traces (and thereby to a corresponding sensor) and detachably connectible to a mating conductive fixture located on the DED. The mating terminals may comprise electromechanically mating, electrically conductive members such as snaps or other types of fasteners or fixtures providing secure mechanical mating and high integrity, high reliability transfer of signals and/or data. In some embodiments, easy and secure mating of the terminals may be enhanced using magnetic mechanisms or other types of mechanisms that help users to properly connect/disconnect the mating terminals with minimal effort.

The DED, in addition to having data recording, processing and/or analysis capabilities, may incorporate an energy source such as a battery providing energy for data recording, processing and/or analysis, as well as providing energy for operation of one or more of the sensor(s). The energy source is preferably a rechargeable and/or replaceable battery source or another energy source. The DED generally provides a lightweight and water-tight enclosure for the data collection and processing electronics and (optional) energy source and provides receiving terminals that mate with the transfer terminals connected to the sensor(s) for conveying data from the sensors to the dedicated electronic device.

Dedicated electronic devices having signal receipt terminals that mate with the signal transfer terminals associated with the substrate may take a variety of form factors, depending on the form factor of the underlying sensing substrate and/or the conditions and location of the device during use. In some embodiments, the DED is provided as a bendable or partially bendable device that can be shaped, as desired, to fit comfortably on and closely to body surfaces having different configurations and sizes. When sensors are incorporated in a sock-like form factor for monitoring conditions sensed at the foot, for example, the signal transfer terminals may be arranged in proximity to one another in an ankle region of the sock, and the DED may have the curved form factor of a band that extends partially around the ankle or lower leg and attaches to the underlying signal transfer terminals and sock substrate along a front and/or side portion of the user's ankle or lower leg. A DED provided in the form of a curved band for mounting to an ankle, for example, may be at least partially flexible so that it fits, comfortably and functionally, on men's and women's ankles and on ankles having different sizes and shapes, providing connection to the sensor transfer terminals provided in a sock or anklet form. In some embodiments, a partially or fully bendable DED may be used in both a curved and a straightened (e.g., flat or substantially flat) form, depending on the location of sensor transfer terminals provided on an underlying substrate.

When sensors are incorporated in a garment, or in a wrap or band, the signal transfer terminals may be arranged at or near an exposed portion of the garment, wrap or band following its application to an underlying anatomical structure or body surface, and the DED may be provided as a band or a tab or a dongle-like or capsule-like device having aligned signal receipt terminals that mate with underlying signal transfer terminals. The DED may be provided as a substantially flexible or a substantially rigid component, depending upon the application, and it may take a variety of forms. A DED may be provided in the form of a button or dongle or another type of housing that may be permanently or detachably mounted to a user, to footwear worn by the user, to a garment worn by the user, to an accessory worn by the user, or the like.

The DED preferably communicates with and transfers data to one or more external computing and/or display system(s), such as a smartphone, computer, tablet computer, dedicated computing device, medical records system or the like, using wired and/or wireless data communication means and protocols. The DED and/or an external computing and/or display system may, in turn, communicate with a centralized host computing system (located, e.g., in the Cloud), where further data processing and analysis takes place. A schematic diagram showing one embodiment of DED components providing communication with one or more external electronic devices is shown in FIG. 5. Substantially real-time feedback, including data displays, notifications, alerts and the like, may be provided to the user, caretaker and/or clinician according to user, caretaker and/or clinician preferences.

In some embodiments, the DED may store the data temporarily to a local memory, and periodically transfer the data (e.g., in batches and/or chunks) to the above mentioned external computing and/or display system(s). Offline processing and feedback, including data displays, notifications and the like may be provided to the user, caretaker, and/or clinician according to user, caretaker and/or clinician preferences.

In operation, an authentication routine and/or user identification system matches the DED and associated sensing system (e.g., the collection of sensor(s) associated with an underlying substrate) with the user, caretaker and/or clinician, and may link user information or data from other sources to a software- and/or firmware-implemented system residing on the external computing system. The external computing device may itself communicate with a centralized host computing system or facility where data is stored, processed, analyzed, and the like, and where output, communications, instructions, commands, and the like may be formulated for delivery back to the user, caretaker and/or clinician through the external computing device and/or the DED.

Calibration routines may be provided to ensure that the DED and connected related sensor system are properly configured to work optimally for the specific user. Configuration and setup routines may be provided to guide the user (or caretaker or medical professional) to input user information or data to facilitate data collection, and various protocols, routines, data analysis and/or display characteristics, and the like, may be selected by the user (or caretaker or medical professional) to provide data collection and analysis that is targeted to specific users. Specific examples are provided below. Notification and alarm systems may be provided, and selectively enabled, to provide messages, warnings, alarms, and the like to the user, and/or to caretakers and/or medical providers, substantially in real-time, based on sensed data.

In fitness and footwear fitting applications, additional information indicating specific footwear models owned and worn by the user may be provided. In one embodiment, for example, a user profile interface may be pre-populated with different footwear brands and models, and the user may have options for selecting footwear the user owns and wears by brand, model and size, as well as the frequency and type of usage, and the like. The user may have an option to rate attributes of specific footwear, including comfort, price, perceived value, and the like. Additional, more detailed information relating to the user's experience of specific footwear may be collected, such as the user's subjective fit opinions (e.g., length fit, width fit, heel fit, arch style or fit, support, adherence and or compression, subjective comfort, hotspots experienced during use, and the like). This information may be collected and curated, along with objective force and/or pressure and/or shear measurements and or temperature collected while the user wears identified footwear and while the user participates in identified or identifiable activities while wearing the footwear. Data processing and analysis techniques may be used to correlate subjective user fit impressions to objective footwear pressure data, and to draw conclusions regarding any particular user's subjective fit preferences and requirements. This data, in turn, may be used to generate user-specific recommendations for footwear brands, models, sizes, and the like, that are likely to match the user's subjective fit preferences and requirements.

Collection of this type of data from users across various populations allows other aspects of a host system to characterize specific footwear in accordance with the feedback provided. This type of footwear characterization and user experience is useful for footwear designers and manufacturers and may be used to improve footwear fit, performance and interior design across various user populations. It may also be used to make footwear recommendations tailored to specific users based on their foot type, footwear attributes, subjective and objective footwear experiences, and types of activities. Similar features and interface options may be provided to characterize for various types of fitness training, medical monitoring and health and wellness applications. Detailed information may be collected, for example, relating to a user's wearable accessories (gloves, clothing, head gear, etc.), sports and fitness equipment (golf clubs, bats, boxing gloves, etc.), and subjective user experience data may also be collected. Collection of this data from users across various populations allows the host system to characterize specific user wearables and equipment and make recommendations for wearables and equipment tailored to specific users based on their user profile data.

In some aspects, the present disclosure provides sensing systems and methods that allow a user or a third party to evaluate the subjective comfort of specific footwear worn by the user. In this embodiment, sensor systems comprising pressure sensors may be worn by a user while the user wears footwear, and pressure and/or force and/or shear data may be collected during the user's engagement in various activities. The pressure and/or force and/or shear data collected may be associated or correlated with the user's subjective comfort impressions to provide a user fit and comfort profile that may reflect the user's fit and comfort preferences relating to specific footwear types, styles, brands, and the like. User fit and comfort profiles may facilitate and supplement in-person fitting sessions and/or remote purchasing experiences (e.g., via e-commerce) and facilitate matching of a user's profile to specific footwear types, styles, brands, sizes, and the like. These sensing systems and methods may be implemented, for example, by a retail outlet, a footwear representative, an e-commerce site or the like, to evaluate and provide user-specific fit and comfort data to facilitate improved footwear fitting, increase user satisfaction, and reduce footwear and/or garment returns.

In another aspect, the present disclosure relates to sensor systems and methods that may be implemented for example, by footwear designers and manufacturers, to inform and improve footwear design, fit and comfort for particular user groups. Knowledge of user fit and comfort profiles may, for example, facilitate the design and manufacture of footwear that provides better fit and comfort characteristics across a wider range of users. Knowledge of user fit and comfort profiles may, additionally, facilitate the design and manufacture of footwear customized for individual users, or for user groups sharing common fit and comfort attributes.

In another aspect, user data sets collected using sensor systems of the present disclosure may be assembled and curated in a library containing data sets collected from multiple users. In this aspect, any particular user's data may be compared to data collected across large collections of users, and/or to contextual and/or biometric data categorized as similar. Algorithms may be designed and applied to provide user-specific feedback relating to the user's relationship to collections of similar users and/or to similar sets of contextual and/or biometric data. Comfort, preference and fit recommendations may be based on this comparative data analysis.

Based on this data analysis, personalized recommendations relating to footwear-, prosthetic- and garment-fitting may be provided. In some aspects, for example, systems and methods described herein allow a user, clinician, or the like, to accurately evaluate the comfort of footwear, compression garments, prosthetic devices, and the like, and to evaluate the presence and location of hotspots and quantitate pressure, force and/or shear exerted on body surfaces. In some aspects, systems and methods disclosed herein may be used to facilitate the selection of footwear, garments, close-fitting accessories, and the like, under circumstances that don't permit a user to be fit, in person, to footwear, garments, close-fitting accessories, or the like. The systems and methods described herein may be used, for example, to facilitate fitting of footwear and close-fitting accessories available only in remote locations inaccessible to the user, or through e-commerce sites, or the like.

BRIEF DESCRIPTION OF THE DRAWINGS

FIG. 1A shows a side view, FIG. 1B shows a top view; FIG. 1C shows a bottom view, and FIG. 1D shows a front perspective view illustrating potential regions for sensor location according to one embodiment of a footwear comfort and fitting sensing system.

FIG. 2A shows the plantar surface of the carrier layer having associated sensors; FIG. 2B shows another area of the carrier layer where conductive traces terminate in conductive and common terminals.

FIG. 3A shows a perspective view of a foot or last showing potential sensor locations; FIG. 3B shows a bottom view; and FIG. 3C shows a "rear" view illustrating a potential sensor location on the heel.

FIGS. 4A and 4B illustrate a pressure/shear sensor located under the ball of the foot; and FIG. 4C illustrates two pressure/shear sensors, one located under the ball of the foot and on located in the area of the calcaneus.

Figure 1A:
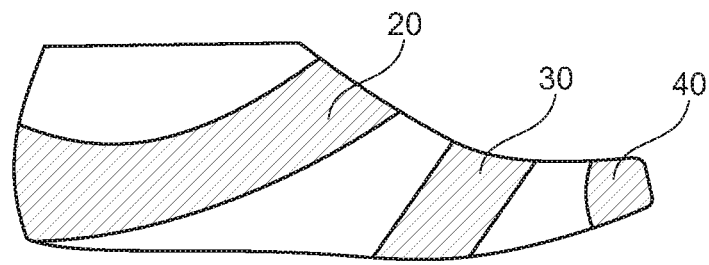
FIGS. 1A, 1B, 1C and 1D show diagrams illustrating sensor locations for sock sensor systems designed for use in footwear fitting applications.
Figure 1B:
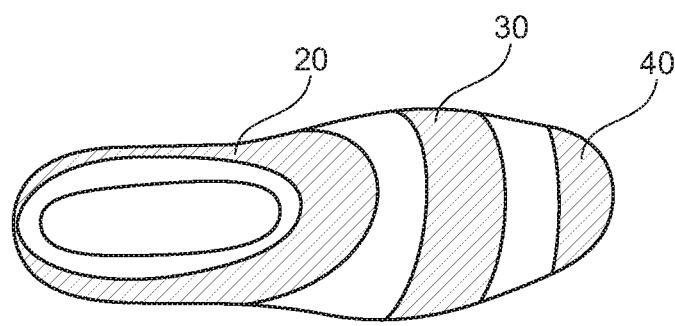
Figure 1C:
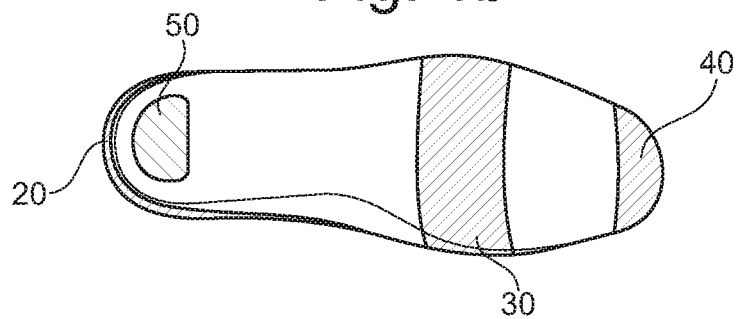
Figure 1D:
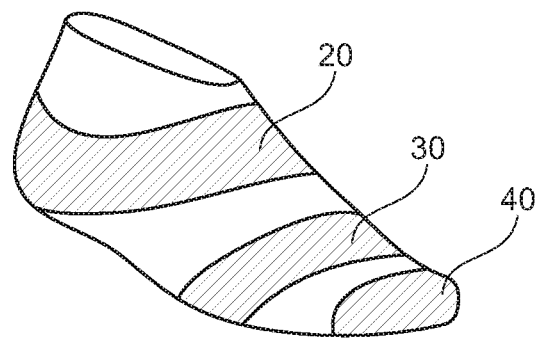

It will be understood that the appended drawings are not necessarily to scale, and that they present simplified, schematic views of various aspects of systems and components of the present invention. Specific design features, including sensor types, dimensions, orientations, locations and configurations may be modified, for example, for use in various intended applications and environments. Other system components may be included to provide additional features, or to tailor systems and methods for various applications.

DETAILED DESCRIPTION

In one embodiment, systems incorporating pressure sensors, traces and terminals may be associated with a close-fitting garment or portion of a garment, such as a sock, a compression garment (sock, sleeve, band or the like), a shirt, belt, pants, or another type of garment or substrate. Pressure sensors used in footwear and sock applications may comprise resistive sensors capable of detecting (relative and/or absolute) levels of pressure and/or force and/or shear at one or more identified spatial areas of the foot. Based on the detected pressure, force and/or shear at one or more areas of the foot during rest or during engagement in different activities, trends in those parameters over one or more monitoring period(s), conclusions relating to footwear comfort, fit, the presence and location of hot spots generated by force and/or pressure and/or shear, the user's gait characteristics, and the like, may be drawn and may be communicated to the user, caretaker and/or clinician, essentially in real time. In addition, notifications, alerts, recommended actions, and the like may also be communicated to the user, caretaker and/or clinician based on the data analysis.

Various aspects of sensor placement are described below with specific reference to socks incorporating pressure sensors and sensing systems, and with specific reference to footwear-fitting applications. It will be appreciated that the sensor systems and methods disclosed herein are not limited to these applications and may be applied in numerous other applications. The pressure sensor placement described herein may be used, for example, for other applications such as gait analysis and monitoring, fitness and sports applications, and the like. Other substrates such as garments or objects incorporating pressure sensors and sensing systems and methods as disclosed herein may also be implemented for various purposes.

Several foot locations for pressure sensing during static and dynamic motion are important to evaluate footwear comfort and fit, including the following: the instep; the heel clip point; under-ankle bones (medial and lateral); the ball area of the underfoot; dorsal area of the forefoot (e.g., the metatarsal-phalangeal joint region); and various locations (dorsal, plantar and front) area of the toe box. Pressure sensing at the dorsal midfoot area (e.g., over the navicular, cuboid and cuneiform bones) during static and dynamic gait may also be important. Methods and systems disclosed herein preferably sense force and/or pressure and/or shear during a user's gait at at least three of these locations during at least one static and/or dynamic gait interval, more preferably at at least four of these locations during at least one static and/or dynamic gait interval; more preferably yet at at least five of these locations during at least one static and/or dynamic gait interval.

In some embodiments, foot girth measurements (e.g., overall foot length, as well as foot width and foot girth at one or more locations) are provided and used, in combination with static and/or dynamic gait pressure and/or force and/or shear measurements to assess footwear comfort and fit. In some embodiments, user gait characteristics (e.g., tendency to supinate, pronate, etc.) may be evaluated and used, in combination with one or more other static and/or dynamic gait characteristics, to assess footwear comfort and fit, and to recommend footwear having desirable characteristics. In some embodiments, user gait characteristics may be analyzed, along with a user's comfort profile, to assess footwear comfort and fit, and to recommend footwear having desirable characteristics.

FIGS. 1A-1D illustrate a plurality of regions in the form of bands in relation to a foot where pressure/shear sensors are appropriately placed (in a sock form factor, for example) for purposes gait and footwear evaluation. One sensing region includes a region located in an upper, front foot region in the area of and below the ankle, extending laterally and medially in a band below the ankle area and across the back of the heel area, shown in FIGS. 1A-1D as sensor band 20. A second sensing region, illustrated as sensor band 30, includes a joint area on the top of the foot extending around the foot and underneath in the ball area of the foot. A third sensing region, illustrated as sensor area 40, includes a toe-box area, including the top and ends of the toes and extending underneath the toes. Yet another sensing region 50 may extend underneath the heel. The sensing regions, as illustrated, may be from about one inch to about three inches wide, and may have regular or irregular edges and configurations. In some embodiments, sensor bands comprising resistive e-textile pressure sensitive material may be provided substantially co-extensive with the sensing regions illustrated. In some embodiments, sensor bands comprising resistive e-textile pressure sensitive material may be provided as discontinuous elements within the sensing regions illustrated. Each of the pressure/shear sensors may be electrically associated with a conductive trace, as described in the disclosure provided above, or otherwise as known in the art. Additional sensors may be used in connection with socks, and other types of sensors, including heat sensors (e.g., thermocouples), moisture sensors, and the like, may also be incorporated in socks having pressure/shear sensors as described herein.

In some embodiments, at least one discrete pressure/shear sensor is generally provided within the area of each of the four sensing regions illustrated in FIGS. 1A-1D. In some embodiments, multiple, spatially discrete pressure/shear sensors may be provided in each of the four sensing regions illustrated in FIGS. 1A-1D. The spatial extent or surface area of each pressure sensor may vary, and pressure sensors provided at different spatial locations may have different sensing surface areas.

Figure 2A:
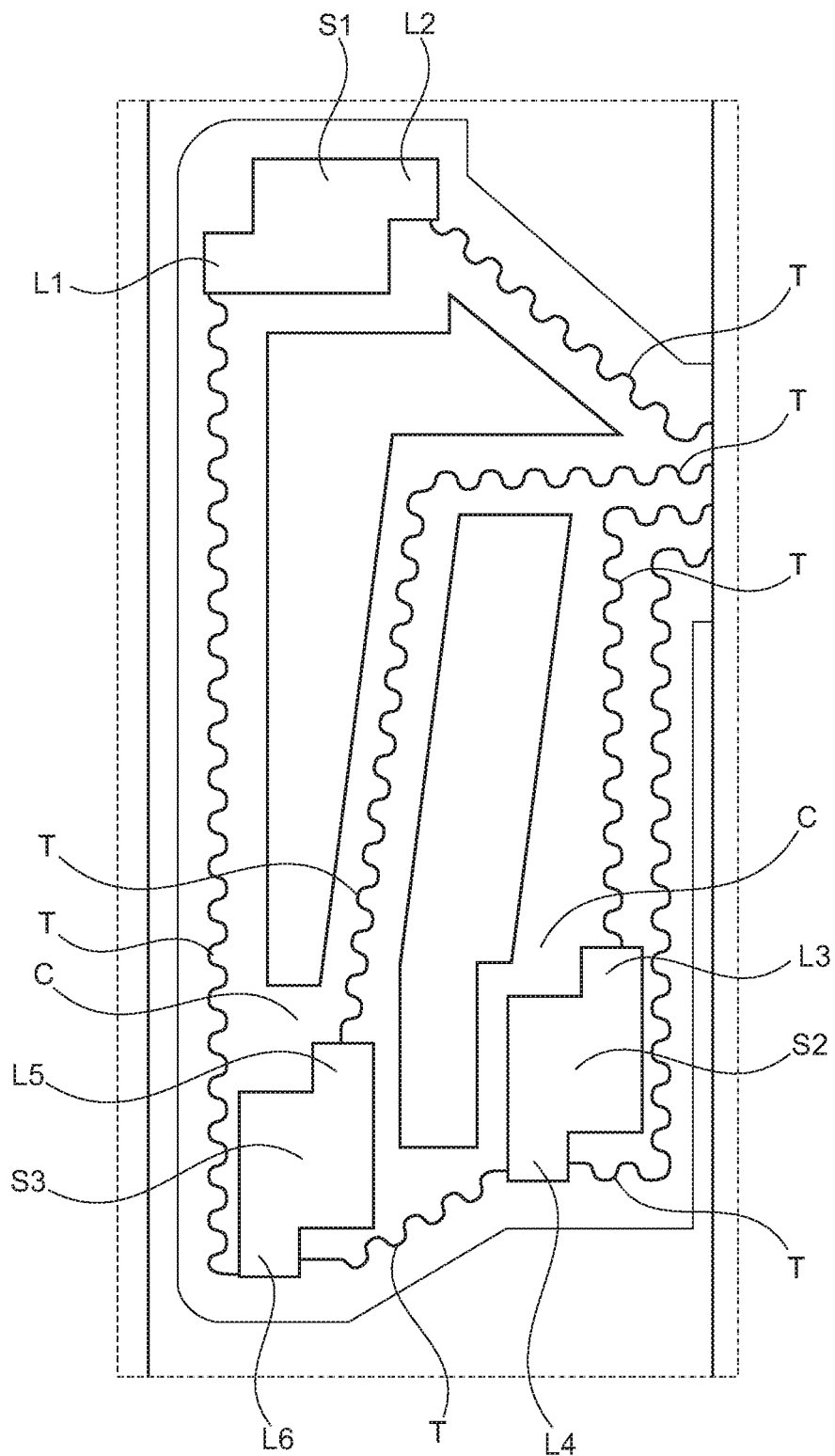
FIGS. 2A and 2B show exemplary sensor assemblies in which discrete pressure/shear sensors and corresponding leads are operatively coupled to conductive traces, and the sensor(s), leads and traces are associated with a flexible, substantially electrically non-conductive carrier layer.
Figure 2B:
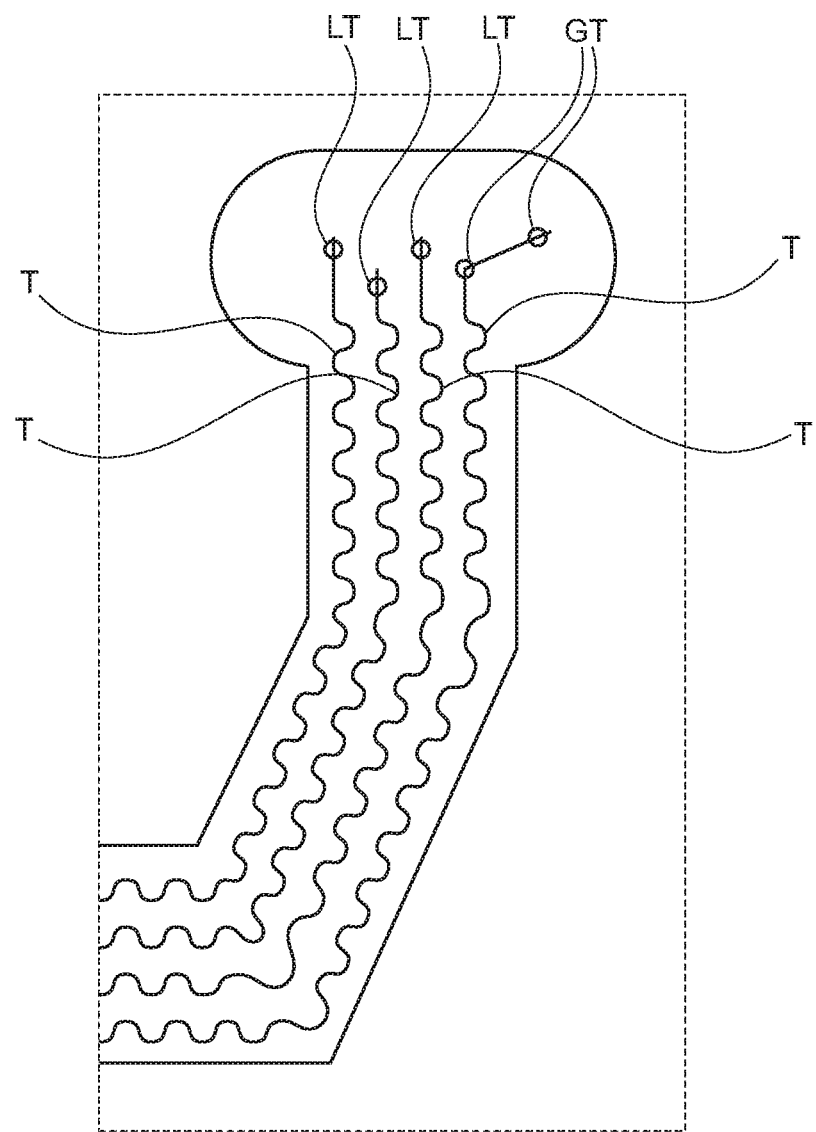

FIGS. 2A and 2B illustrate exemplary sensor assemblies in which discrete pressure/shear sensors S1, S3, S3 and corresponding leads (L1-L6) are operatively coupled to conductive traces T, and the sensor(s), leads and traces are associated with a flexible, substantially electrically non-conductive carrier layer C. The carrier layer C underlies (or overlies) the sensors, leads, traces and terminals and may be provided as a continuous layer (as shown in FIG. 2B), or may have a cut-out configuration (as shown in FIG. 2A). Sensors may be positioned in different areas, such as a plantar region of the foot (see, FIG. 2A), and conductive traces T provide an electrical pathway between each sensor and a conductive terminal CT or ground terminal GT (see, FIG. 2B), which may be located at a common area, such as at an ankle region or another region of the foot for coupling to mating terminals of a DED. In the illustrative embodiment shown in FIGS. 2A and 2B, the sensor assembly comprises sensors and leads that may be positioned at a plantar region of a sock (or footwear, footwear accessory, etc.), while the traces extend from the sensor leads in the plantar region to conductive and ground terminals located in a different region of the sock (or footwear, footwear accessory, etc.).

Resistive pressure and/or shear sensors and leads may comprise e-textile materials, as described above, or other types of flexible resistive materials, such as resistive thermoplastic elastomers (TPEs), resistive inks, resistive silicon-containing materials, or other materials capable of manifesting a dielectric behavior. Similarly, conductive traces may comprise conductive e-textile materials, conductive yarns or threads, conductive metallic materials, or other types of flexible conductive materials, such as conductive thermoplastic elastomers (TPEs), conductive inks, conductive silicon-containing materials, and the like.

When pressure sensors and associated components are associated with a non-conductive carrier layer to form a sensor assembly, the carrier layer may be bonded or adhered or otherwise associated with a substrate, such as a sock, a garment, footwear or a footwear accessory. Flexible and substantially electrically non-conductive carrier layers may comprise materials such as polyvinyl chloride materials, silicone-containing materials, and the like. In some embodiments, assemblies of sensors, leads and traces may be provided on a single carrier layer; in alternative embodiments, assemblies of sensors, leads and traces may be sandwiched between two carrier layers to isolate the sensors and associated components from interference produced by contact with skin, from moisture, and to provide higher durability. Carrier layer(s) may comprise a very thin, flexible and substantially moisture resistant membrane-like structure. Signal transfer terminals and ground terminals may likewise be associated with a carrier layer, as shown in FIG. 2B.

Thus, socks or footwear or footwear accessories (e.g., insoles, liners, booties, and the like) may include one or more discrete pressure/shear sensors provided in a toe box area of the foot, such as in an upper toe box portion that overlies a dorsal portion of toes, an end portion of the toe box that overlies the distal ends of the toes, and/or a plantar portion of the toe box that underlies the toes. In some embodiments, as mentioned above, a toe box sensor may be provided as a substantially continuous sensor over this area; in some embodiments, multiple (associated or independent) pressure sensors may be provided at multiple locations within the toe box area. Socks or footwear or footwear accessories may alternatively or additionally include at least one forefoot sensor having a continuous or multiple sensor configuration that encompasses the metatarsal and/or metatarsal-phalangeal joint region on the dorsal side of the foot and the ball region on the plantar foot surface. Socks or footwear or footwear accessories may alternatively or additionally include at least one instep and/or heel sensor having a continuous or multiple sensor configuration. Heel sensors may be provided at the back region of the heel and/or underneath the heel.

Figure 3A:
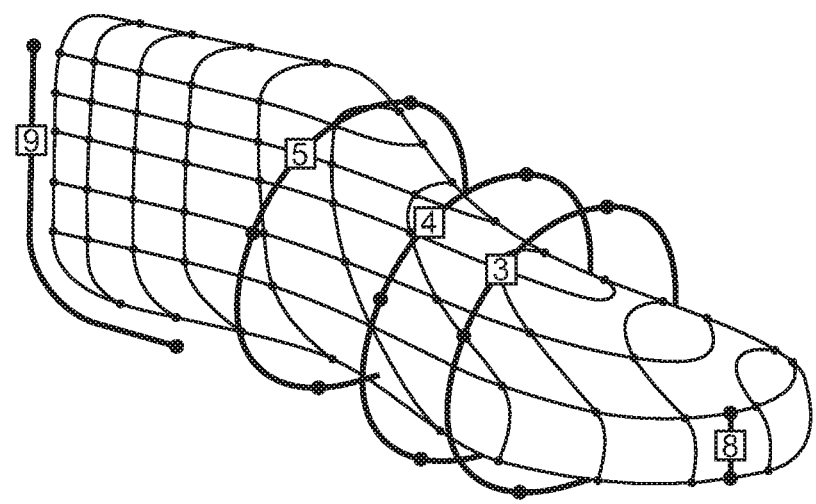
FIGS. 3A, 3B and 3C show additional diagrams illustrating potential regions for sensor location according to additional embodiments of a footwear comfort and fitting sensing system.
Figure 3B:
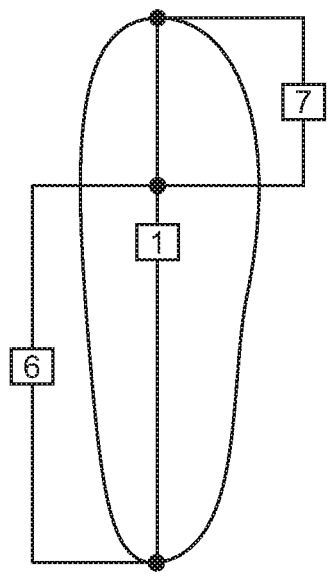
Figure 3C:
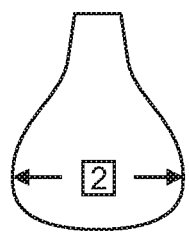

FIGS. 3A-3C illustrate another schematic diagram illustrating exemplary pressure/shear sensor positioning for gait and footwear monitoring purposes. One or more pressure/shear sensors may be provided at or in proximity to the locations (e.g., bands, segments, etc.) identified as regions 1-9 in FIGS. 3A-3C. Area 1, shown in FIG. 3B, is in a plantar region of the foot, in a forefoot or arch area. Area 2, shown in FIG. 3C, is at the calcaneus region. Regions 3, 4 and 5 extend around the foot in forefoot, midfoot, foot dome and arch regions. Region 6 is at the plantar heel region and region 7 is at a plantar region under one or more toes. Region 8 is at a front portion of the toe region and region 9 extends along and underneath the heel region. Pressure/shear sensors are preferably provided at at least 3 of the illustrated regions, more preferably at at least 4 or at least 5 or at least 6 or at least 7 or at least 8, or at each of the nine regions shown, including at the back of the heel, the front of the toes, the center of the arch, and medial and lateral sides of the foot, and the foot dome. In some embodiments, multiple sensors may be located in various of the identified regions.

Several pressure (and/or force and/or shear) monitoring locations and measurements may be important to and may be used in connection with static and dynamic gait monitoring and footwear fitting applications, including the following: (1) seat and in-step, including one or more of pressure difference over the instep during gait, pressure difference at the heel clip point during gait, and pressure from the under-ankle bones (i/s and o/s) during gait; (2) ball and joint, including one or more of joint girth measurements (e.g., overall length, width and girth), pressure difference at the underfoot (ball area) during gait, and pressure difference at the over-foot (dorsal area) caused by upper flexing during gait; and (3) toe box, including pressure difference at the toe area during gait.

Pressure sensor systems, as described herein, preferably provide analog signals to a data processing and analysis system that allow the system to identify the following: (1) when pressure is applied on the surface of the sensor (using appropriate gating techniques); (2) when pressure is not applied on the surface of the sensor (using appropriate gating techniques) and (3) the temporal duration of the relative amount of pressure applied on the surface of the sensor. Pressure sensor and analysis systems may additionally provide data relating to the intensity of pressure applied on the surface of the sensor in comparative and/or absolute terms, the intensity of pressure applied to discrete areas of the surface of the sensor in comparative and/or absolute terms, and may detect additional parameters, such as shear, as described herein.

Figure 4A:
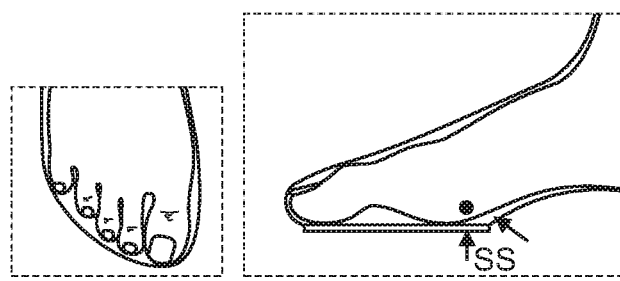
FIGS. 4A-4C show diagrams illustrating the use of shear force detection and shear measurements that may contribute to footwear comfort and fitting sensing systems.
Figure 4B:
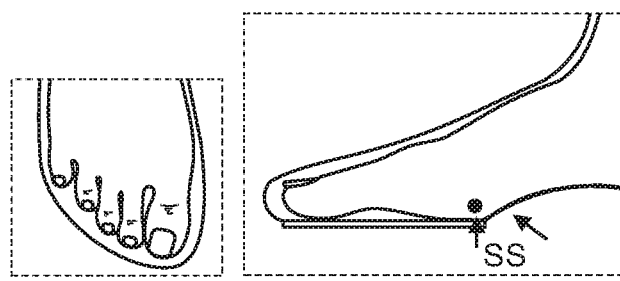
Figure 4C:
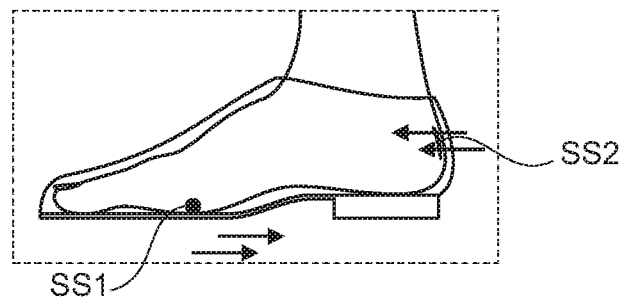
Figure 5:
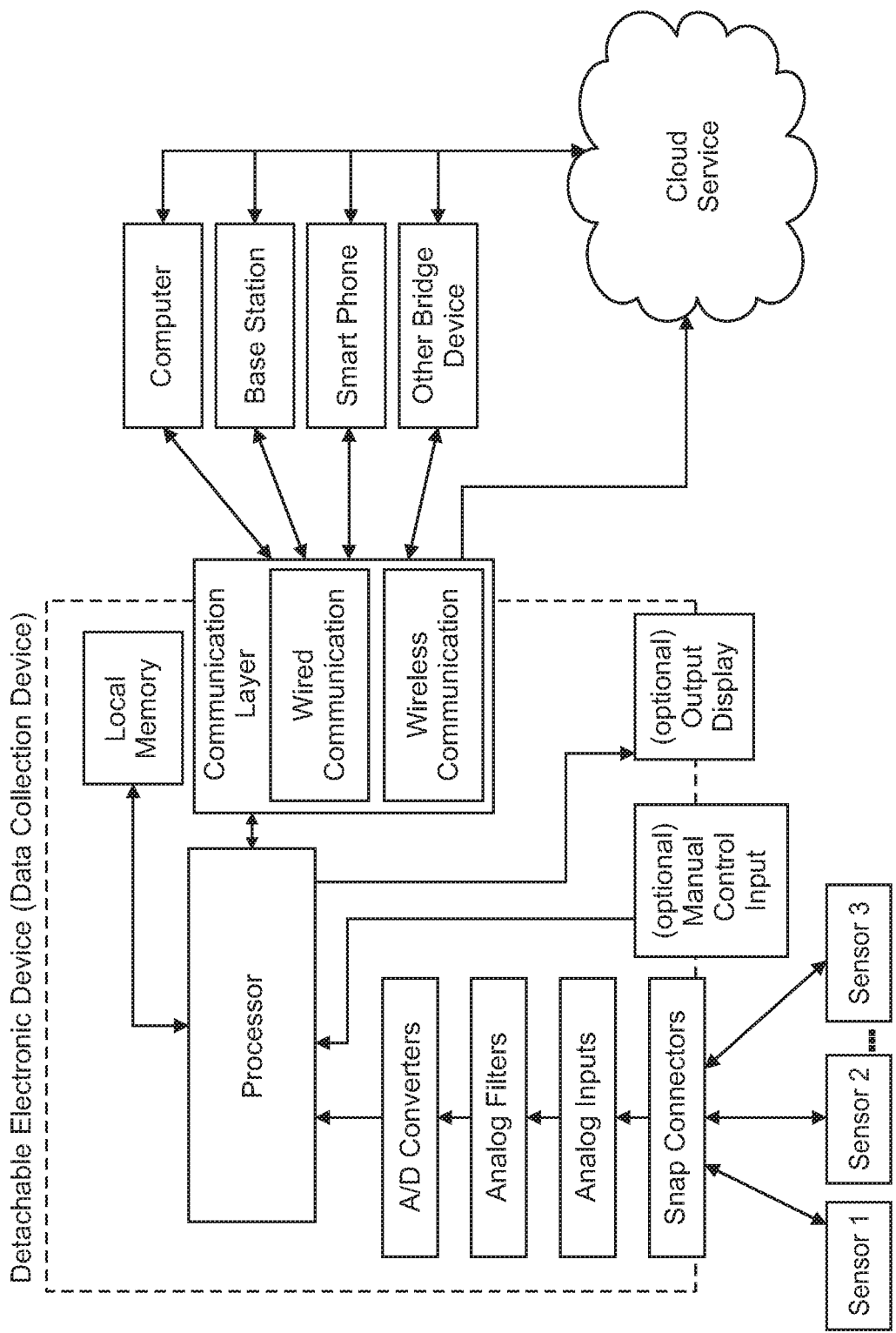
FIG. 5 shows a block diagram illustrating basic components of an exemplary data collection device and illustrating its interface with sensors provided in a substrate, external devices, and a centralized host system maintained, for example, in the Cloud.

FIGS. 4A-4C illustrate schematic diagrams describing shear detection, such as detection of anterior/posterior, medial/lateral and/or oblique/parallel foot movement, and how it may affect proper foot dynamics and footwear fitting. Shear detection may be accomplished by detection of sliding movement using the pressure sensors described herein. FIGS. 4A and 4B illustrate a pressure/shear sensor SS located under the ball of the foot that detects pressure and/or shear applied by or to the foot. The foot, and particularly the forefoot, slides backward and forward doing movement in the poor fitting footwear illustrated in FIG. 4A, causing detectable shear at the location of the pressure/shear sensor SS. The forefoot remains more stably positioned in the footwear illustrated in FIG. 4B, producing less detectable shear at the location of the pressure/shear sensor SS. FIG. 4C illustrates two pressure/shear sensors SS1, SS2, located under the ball of the foot and in the area of the calcaneus. The foot, and particularly the forefoot and heel, slide backward and forward doing movement in the poor fitting (too large) footwear illustrated in FIG. 4C, causing detectable shear at the locations of the pressure/shear sensors SS1, SS2. Shear produced at identifiable locations on a user's foot may create hotspots and damage to the plantar surface of the foot, as well as at other foot locations. Detection of shear during footwear fitting can result in identification of better fitting footwear, which generally and desirably reduces the incidence and severity of shear and the consequent hotspots and injury.

While specific examples of sensor systems and pressure sensor placement has been described with reference to garments having a sock form factor, it will be appreciated that pressure sensors may be used with (and/or applied to) other types of wearable garments (e.g., underwear, t-shirts, trousers, tights, leggings, hats, gloves, bands, and the like), and dedicated electronic devices having different configurations may be designed to interface with a variety of sensor systems embodied in different types of garments. Similar types of flexible e-textile sensors may be applied to or associated with a wide variety of non-conductive underlying flexible substrate materials, including woven and non-woven materials, and incorporated in a variety of sensor systems. The sensor systems interface with one or more intermediate electronic devices, as described above, and data may be processed and analyzed, with feed back provided by a centralized host system.

In some embodiments, feedback such as 2-dimensional and/or 3-dimensional pressure and/or force and/or shear maps of the user's foot provides visualization of areas of high and low pressure, force and/or shear during sitting, standing and various activities. 2D and 3D maps may be color coded to highlight areas of higher intensity and may be streamed to a display device to provide a real-time feedback and mapping during movement. In some embodiments, raw force and/or pressure and/or shear data collected during various user activities (sitting, standing, moving) may be processed and manipulated to display gait pressure curves determined independently at the various sensors or at spatial locations within each sensor. Various sensor data may be combined, averaged, analyzed, etc. to provide different types of feedback in different feedback formats.

Although these specific embodiments have been illustrated and described with reference to the wearable substrate having a sock form factor, it will be appreciated that these specifically disclosed embodiments are non-limiting and the sensors, leads, traces and terminals, as well as different types of DEDs may be adapted for use in other types of garment and non-garment applications.

In one exemplary methodology of the present disclosure, a garment, independently positionable sensing system, bandage or the like, having one or more sensing systems as described herein, is positioned on a user with sensor(s) positioned in proximity to a body area desired to be monitored. A dedicated electronic device is mounted to/on or associated with signal transfer terminals of the sensing system and an authentication protocol is initiated to match the garment/sensing system to the user. The authentication protocol optionally loads user data, profile information, and the like, to one or more hosted systems, such as a centralized data processing and analysis facility, a medical records facility, a caretaker system, or the like. Sensor calibration may then be conducted based on user-specific information, conditions, and the like, and thresholds, limits or specific ranges, monitoring protocols, notifications, alerts, and the like may be selected by the user, a caretaker, clinician, or by the system to apply user-specific monitoring routines, parameters, and the like. Intermittent or substantially continuous user monitoring may then be initiated, with monitoring data and results provided to the user, a centralized data processing and analysis facility, a medical records facility, a caretaker system, clinician dashboard, footwear or garment manufacturer, and the like. Changes and updates to monitoring protocols may be implemented based on monitoring feedback, changes in user conditions, etc.

In one specific example of recommendations made based on clustering, consider the following scenario: "Provide the best fitting shoe recommendation for a specific customer based on the entire population data." The assumption is that people with similar anatomical features will experience similar comfort or pain levels in wearing a shoe. Therefore, individuals having similar individual foot and body structural features provide the best basis for footwear fit predictions.

Consider a user (or foot) profile with the following features: Gender, Age, Weight, Height, Foot Size, Arch Type, Pronation Type, Prevalent Activity type, intensity, frequency, and the like. Let's also consider the following information provided by (some or all) users: Brand (make, model) of shoes worn; subjective fitting information, including Size Fit, Width Fit, Arch Support, Comfort, and Frequency of Usage. The system will cluster the user population based on the user (foot) profile data. The resulting clusters identify groups having affinity (similar characteristics) across selected data categories. Depending on the number of features we select in a specific query, different groups can result (e.g. subjects [male, age 40, over-pronating] vs. [male, age 40, over-pronating, size 10.5]). An additional classification may cluster the shoes, in relation to users, based on the subjective fitting information provided by each user. A ranked list of shoes may be assembled based on the fitting information for each specific cluster of users and used to provide user-specific feedback.

For example, let A, B, C be three clusters of users in our population. Let S1, S2, . . . SN be a set of shoes that the population has come to try/wear. For each cluster, the collection of shoes SJ . . . SN may be ranked based on relative relevance of such shoes for the sub-population of users in the cluster. For example, S1 is recommended favorably by 5 users in cluster A, 2 users in cluster B, 0 users in cluster C. S2 is recommended favorably by 3 users in cluster A, 2 users in cluster B, I 0 users in cluster C. S3 is recommended favorably by I user in cluster A, 5 users in cluster B, 2 users in cluster C. Also, S1 is negatively recommended by I users in cluster A, I users in cluster B, 3 users in cluster C. Assuming, for the sake of simplicity, that a favorable recommendation counts as +1, while a negative recommendation counts as −1. The resulting ranked list for cluster A is (S1, S2, S3) (total rank. −4, 3, 1); the resulting ranked list for cluster B is (S3, S2, S1) (total rank: 5, 2, I). The resulting ranked list for cluster C is (S2, S3) (total rank: 10, 2, −3). The calculation of relevance for the ranking algorithm is generally more sophisticated, because the evaluation of the shoe is more granular (using, for example, a rank of 1 to 5 for each of the subjective fitting attributes assigned by each user on a shoe).

After the classification is performed, a user can receive shoe recommendations simply by providing their foot profile. The recommendation will be accurate as long as enough data points (i.e., a sufficient data population) are available in the knowledge base. Users may also be able to provide their own "feedback" data, augmenting the overall knowledge base and altering the clusters and classification for the ranking algorithms.

While the present invention has been described above with reference to specific embodiments and the accompanying drawings in which specific embodiments are shown and explained, it is to be understood that persons skilled in the art may modify the embodiments described herein without departing from the spirit and broad scope of the invention. Accordingly, the descriptions provided above are considered as being illustrative and exemplary of specific structures, aspects and features within the broad scope of the present invention and not as limiting the scope of the invention. The various embodiments described herein may be combined to provide further embodiments. The described devices, systems and methods may omit some elements or acts, may add other elements or acts, or may combine the elements or execute the acts in a different order than that illustrated, to achieve various advantages of the disclosure. These and other changes may be made to the disclosure in light of the above detailed description. It will also be understood that while the above description and the appended claims refer to methods for accomplishing certain tasks and providing certain feedback, the invention and the disclosure also provides means and systems for implementing the described methods using a host system, as described, interfacing with one or more electronic devices.

In the present description, where used, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives, unless otherwise expressly indicated. As used herein, the terms "include" and "comprise" are used synonymously, and those terms, and variants thereof, are intended to be construed as non-limiting. In general, in the following claims, the terms used should not be construed to limit the disclosure to the specific embodiments disclosed in the specification.

We claim:

1. A method for formulating a user-specific footwear fit and comfort profile comprising:
   providing a sensor-enabled sock to the user, wherein the sock has at least three textile pressure sensors associated therewith, wherein such sensors are sandwiched between two carrier layers to isolate the sensors from interference produced by contact with skin and/or moisture, wherein such sensors are connected to signal transfer terminals that are coupled with a data collection device, and wherein such sensors are located in areas of the sock corresponding to at least three of the following areas of the user's foot: the instep; the heel clip point; medial under-ankle bones; lateral under-ankle bones; the ball area of the underfoot; the dorsal area of the forefoot; and a dorsal, plantar and front area of the toe box;

collecting pressure and/or force and/or shear data at the locations of the at least three pressure sensors during movement of the user when the user is wearing the sensor-enabled sock and particular footwear;

collecting subjective fit impressions of the user when the user wears the particular footwear;

analyzing the pressure and/or force and/or shear data collected at the sensor locations and the subjective fit impressions of the user relating to the particular footwear to generate a user-specific footwear fit and comfort profile; and providing fit recommendations for new footwear to the user based on the user-specific footwear fit and comfort profile.

2. The method of claim 1, wherein at least four pressure sensors are located in areas of the sock corresponding to at least four of the following areas of the user's foot: the instep; the heel clip point; medial under-ankle bones; lateral under-ankle bones; the ball area of the underfoot; the dorsal area of the forefoot; and a dorsal, plantar and front area of the toe box.

3. The method of claim 1, wherein at least five pressure sensors are located in areas of the sock corresponding to at least five of the following areas of the user's foot: the instep; the heel clip point; medial under-ankle bones; lateral under-ankle bones; the ball area of the underfoot; the dorsal area of the forefoot; and a dorsal, plantar and front area of the toe box.

4. The method of claim 1, wherein each pressure sensor comprises a material selected from the group consisting of: a resistive textile; a resistive thread; a resistive yarn; a resistive fiber; a resistive thermoplastic elastomer (TPE); a resistive ink; and a resistive silicon-containing material.

5. The method of claim 1, comprising monitoring pressure and/or force and/or shear at two or more of the following locations: (1) seat and in-step; (2) ball and joint; and (3) toe box; and additionally detecting two or more of the following: pressure differences over the instep during gait; pressure difference at the heel clip point during gait; and pressure from the under-ankle bones (medial and lateral) during gait.

6. The method of claim 5, comprising monitoring at least one of the following additional parameters: pressure difference at the ball area of the underfoot during gait, and pressure difference at the dorsal area of the over-foot caused by upper flexing during gait; and pressure difference at the toe area during gait.

7. The method of claim 5, additionally comprising collecting data relating to joint girth measurements.

8. The method of claim 5, comprising acquiring an analog signal relating to pressure and/or force and/or shear at two or more of the specified locations and identifying, at specific times, whether pressure is applied to the location; whether pressure is not applied to the location; and the duration in time of the relative amount of pressure applied to the location.

9. The method of claim 1, additionally comprising providing the new footwear fit recommendations to the user during an in-person footwear fitting session.

10. The method of claim 1, additionally comprising providing the new footwear fit recommendations to the user during a remote purchasing experience.

11. The method of claim 1, additionally comprising collecting foot measurements from the user and using the foot measurements and the user-specific footwear fit and comfort profile to provide recommendations to customize new footwear to fit the user.

12. The method of claim 1, additionally comprising pre-populating a user profile interface with different footwear brands and models and providing a user option for selecting and rating footwear the user owns and wears by brand, model and size.

13. The method of claim 12, additionally comprising reporting user-specific recommendations for footwear brands, models and sizes.

14. A method comprising:

providing a sensor-enabled sock to a plurality of users, wherein the sock has at least three textile pressure sensors associated therewith, wherein such sensors are sandwiched between two carrier layers to isolate the sensor from interference produced by contact with skin and/or moisture, wherein such sensors are connected to signal transfer terminals that are coupled with a data collection device, and wherein such sensors are located in areas of the sock corresponding to at least three of the following areas of the user's foot: the instep; the heel clip point; medial under-ankle bones; lateral under-ankle bones; the ball area of the underfoot; the dorsal area of the forefoot; and a dorsal, plantar and front area of the toe box;

collecting and recording pressure and/or force and/or shear data at the locations of the at least three pressure sensors during movement of each user when the user is wearing the sensor-enabled sock and specific footwear;

analyzing the pressure and/or force and/or shear data;

assembling data sets relating to pressure and/or force and/or shear data collected from each of the plurality of users and generating multiple user data sets;

comparing data collected from individual users to multiple different user data sets of contextual and/or biometric data, wherein the multiple different user data sets include pressure and/or force and/or shear data; and reporting data or recommendations to an individual user based on the comparison with multiple different user data sets of contextual and/or biometric data.

15. The method of claim 14, additionally comprising collecting subjective comfort data from the user when the user wears the sensor-enabled sock with particular footwear.

16. The method of claim 14, additionally comprising: providing personalized footwear recommendations to a user based on multiple user data sets.

17. The method of claim 14, additionally comprising providing user-specific feedback relating to a user's relationship to collections of different users and/or different user data sets of contextual and/or biometric data.

* * * * *